US00PP22608P2

(12) United States Plant Patent
Snoeijer

(10) Patent No.: US PP22,608 P2
(45) Date of Patent: Mar. 27, 2012

(54) ***CLEMATIS* PLANT NAMED 'ZOFOFRI'**

(50) Latin Name: ***Clematis* hybrid**
Varietal Denomination: Zofofri

(76) Inventor: Wim Snoeijer, Gouda (NL)

( * ) Notice: Subject to any disclaimer, the term of this patent is extended or adjusted under 35 U.S.C. 154(b) by 0 days.

(21) Appl. No.: 12/924,461

(22) Filed: Sep. 28, 2010

(51) Int. Cl.
*A01H 5/00* (2006.01)

(52) U.S. Cl. ..... Plt./228

(58) Field of Classification Search ..... Plt./228
See application file for complete search history.

(56) References Cited

OTHER PUBLICATIONS

UPOV-ROM GTITM, Plant Variety Database, 2011/01, Pluto Software, Citation for plant 'Zofofri'.*
UPOV-ROM GTITM, Plant Variety Database, 2011/04, GTI JOUVE Retrieval Software, Citation for plant 'Zofofri'.*

* cited by examiner

*Primary Examiner* — Susan McCormick Ewoldt
(74) *Attorney, Agent, or Firm* — Penny J. Aguirre

(57) ABSTRACT

A new cultivar of hybrid *Clematis*, 'Zodaki', characterized by its floriferous habits, its flowers that are white in color with purple anthers, its primarily upright facing flowers on semi-nodding pedicels with good presentation, its near sterility, and its cold hardiness at least to U.S.D.A. Zone 6.

3 Drawing Sheets

Botanical classification: *Clematis* hybrid.
Variety denomination: 'Zofofri'.

BACKGROUND OF THE INVENTION

The present invention relates to a new and distinct cultivar of *Clematis*, botanically an interspecific hybrid, and will be referred to hereafter by its cultivar name 'Zofofri'. 'Zofofri' is grown as an herbaceous perennial for landscape use or as a terrace pot plant.

'Zofofri' was derived from seedlings raised by the breeder from crossbreeding *Clematis* 'Mrs. George Jackman' (unpatented) pollinated by *Clematis* 'Walenburg' (unpatented). The crossbreeding was done in 2000, the seedling 'Zofofri' was selected was selected as a single unique plant from the batch of seedlings in 2003.

Asexual reproduction of the new cultivar was first accomplished by internodial stem cuttings by the Inventor in Boskoop, The Netherlands in 2003. The characteristics of this cultivar have been determined to be stable and are reproduced true to type in successive generations.

SUMMARY OF THE INVENTION

The following traits have been repeatedly observed and represent the characteristics of the new cultivar as grown outdoors. These attributes in combination distinguish 'Zofofri' from other varieties of *Clematis* known to the inventor.

1. 'Zofofri' exhibits a very floriferous habit.
2. 'Zofofri' exhibits flowers that are white in color with purple anthers.
3. 'Zofofri' exhibits primarily upright facing flowers on semi-nodding pedicels with good presentation.
4. 'Zofofri' has been observed to be essentially sterile; very rarely are any seed is produced.
5. 'Zofofri' is cold hardy at least to U.S.D.A. 6.

'Zofofri' can be most closely compared to its parent plants. 'Mrs. George Jackman', the seed parent, differs primarily from 'Zofofri' in having a much less floriferous habit and in having flowers that are not nodding and pink in color. 'Walenburg', the pollen parent, differs primarily from 'Zofofri' in having flowers that are purple-red in color and in having smaller flowers.

'Zofofri' can be compared to the cultivar 'Huldine' (not patented) and 'John Huxtable' (not unpatented). 'Zofofri' exhibits flowers that are nodding or semi-nodding, nodding flower buds, tepals which are white in color and purple connective. 'Huldine' differs from 'Zofofri' in having flowers that are upright, upright flower buds and the tepals that are white at the upper surface and pale purple at the lower surface, and cream connective. 'John Huxtable' differs from 'Zofofri' in having flowers that are upright, upright flower buds, tepals which are white in color and cream connective.

BRIEF DESCRIPTION OF THE DRAWING

The accompanying colored photographs illustrate the overall appearance and distinct characteristics of *Clematis* 'Zofofri'. The photographs were taken of plants of 'Zofofri' that were grown outdoors for three years in a trial bed in Boskoop, The Netherlands.

Figure 1:
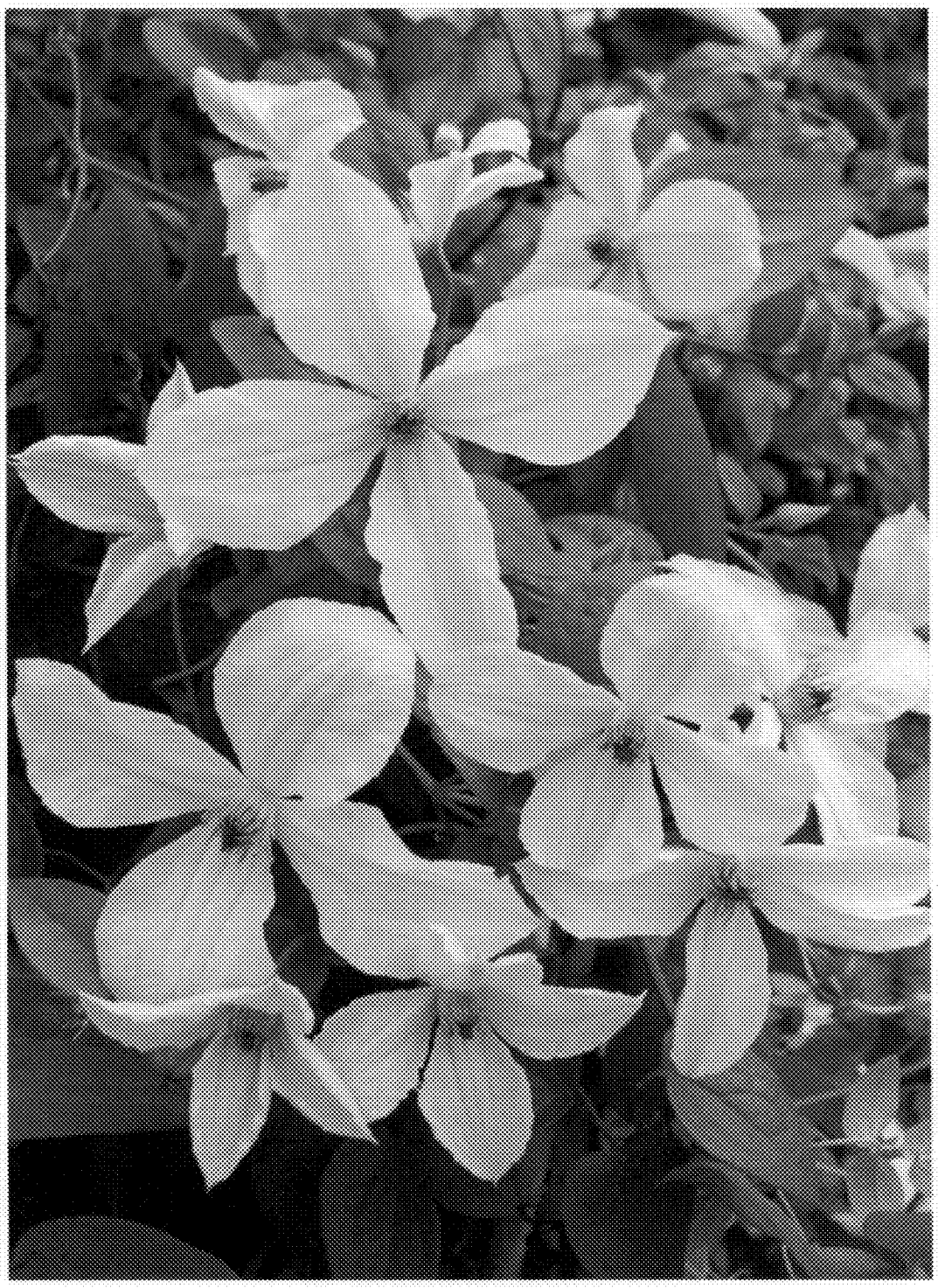
FIG. 1 shows the flowering habit of 'Zofofri'.
Figure 2:
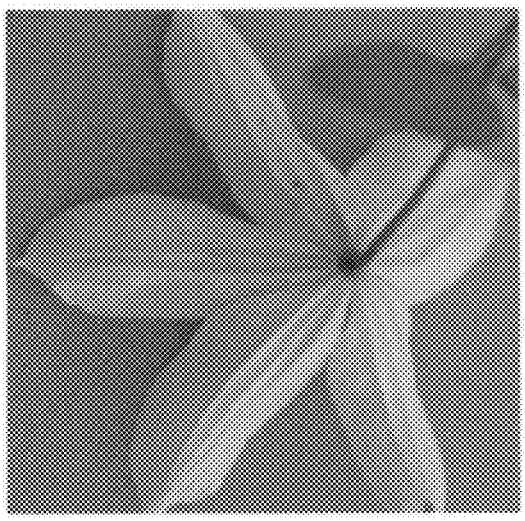
FIG. 2 shows the back of the flower of 'Zofofri'.
Figure 3:
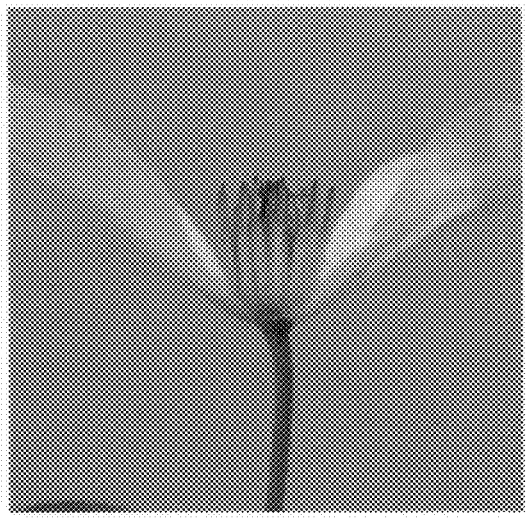
FIG. 3 shows the inside of the flower of 'Zofofri' with a close up of the stamens and pistils.
Figure 4:
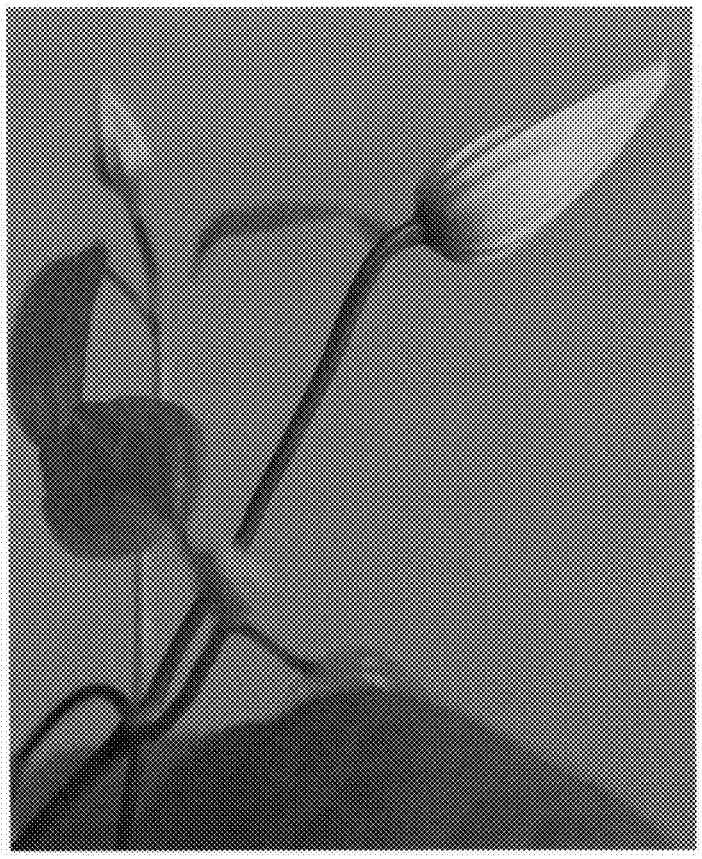
FIG. 4 shows a flower bud of 'Zofofri'.
Figure 5:
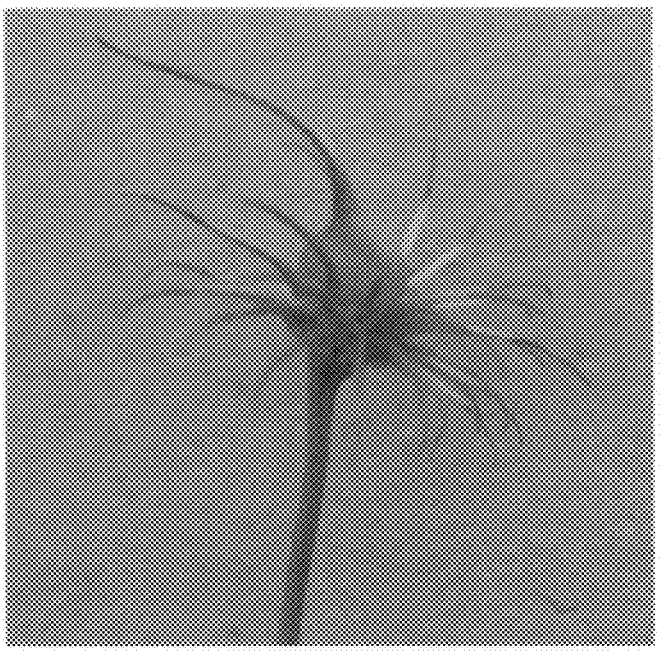
FIG. 5 shows a seedhead of of 'Zofofri'.
Figure 6:
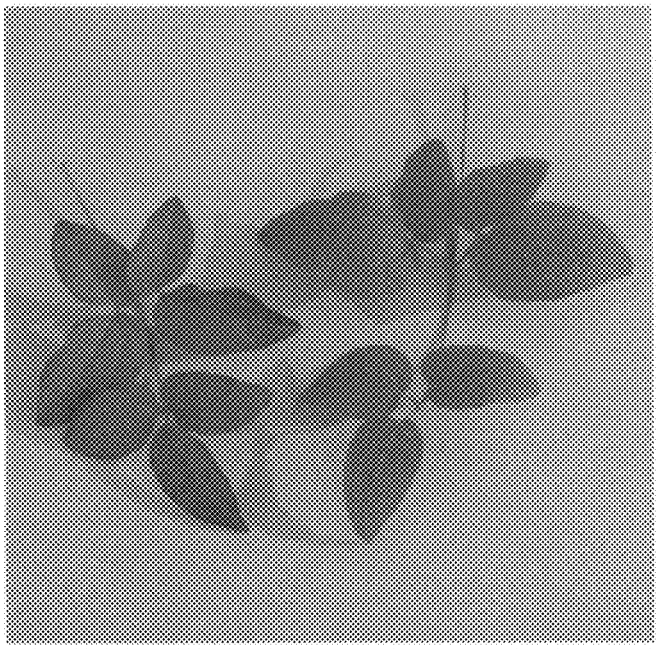
FIG. 6 shows 2 leaves of 'Zofofri'.

The colors of the photographs are as close as possible with the digital photography techniques available, the color values cited in the detailed botanical description describe the colors as accurately as possible of the new *Clematis*.

DETAILED BOTANICAL DESCRIPTION

The following is a detailed description of 3 year-old plants *Clematis* 'Zofofri' as grown outdoors in full sun to semishade at a nursery in Boskoop, The Netherlands. The phenotype of *Clematis* 'Zofofri' may vary with variations in environmental, climatic and cultural conditions, as the cultivar has not been tested under all possible environmental conditions. The color determination is in accordance with the 2001 R.H.S. Colour Chart, London, England, except where general color terms of ordinary dictionary significance are used. The International Nomenclatural Standard is deposited at the Nationaal Herbarium Nederland, Leiden Branch (L).

General description:

*Botanical classification*.—'Zofofri' is classified in the Jackmanii Group of *Clematis*.

*Common name*.—'Zofofri' *Clematis*.

*Parentage*.—Hybrid derived from the female parent *Clematis* 'Mrs George Jackman', pollinated by *Clematis* 'Walenburg'.

*Blooming period*.—Main flowering period of 4 to 6 weeks in summer.

*Plant habit*.—Herbaceous climber.

*Height*.—Three year old plant will be at about 2.5 m height when pruned in late winter.

*Cold hardiness*.—At least to U.S.D.A. Zone 6.

*Culture*.—Moist but well-drained soil in full sun with the roots in the shade.

*Diseases and pests*.—May be susceptible to powdery mildew.

*Root description*.—Fleshy.

Growth and propagation:

*Propagation*.—Internodial soft wood cuttings from vegetative shoots.

*Root initiation*.—Roots develop in 6 weeks in summer under greenhouse conditions.

*Time required for root development*.—75 to 90 days to develop a 5 cm container from a 5 cm cutting.

*Growth rate*.—Moderately vigorous once planted out.

Stem description:

*Shape*.—Round, slightly ribbed.

*Stem color*.—Green 144C but quickly woody brown 165A.

*Stem size*.—Up to 2.5 m in length, about 0.5 cm in diameter.

*Stem surface*.—Sparsely hairy.

*Branching*.—Basal branches.

Foliage description:

*Leaf arrangement*.—Opposite.

*Leaf division*.—Pinnate but sometimes ternate.

*Internode length*.—6 to 15 cm in length.

*Leaf size*.—Up to 15 cm in length and 10 cm in width.

*Leaflet shape*.—Ovate to lanceolate to elliptic.

*Leaflet base*.—Cuneate to oblique.

*Leaflet apex*.—Acute.

*Leaflet fragrance*.—None.

*Leaflet venation*.—Primarily reticulate but not prominent, same color as leaves.

*Leaflet margins*.—Entire or sometimes cleft.

*Leaflet attachment*.—Petioluled with leaf petiole.

*Leaflet surface*.—Upper surface glabrous, lower surface puberulent.

*Leaflet size*.—Up to 7 cm in length and 4 cm in width.

*Leaflet color*.—Upper surface green 144A in color stained with purple N77A in cold weather, lower surface slightly paler green 144B in color.

*Petioles and petiolules*.—Petiole up to 10 cm in length and about 2 mm in width, green 144B in color, glabrous but sparsely hairy at the nodes, petiolule up to 2 cm in length and about 1 mm in width, green 144C in color and sparsely hairy surface, sometimes curling.

Inflorescence description:

*Inflorescence type*.—A 3 to 7-flowered dichasial cyme.

*Inflorescence arrangement*.—Terminal and axillary.

*Inflorescence size*.—Various with flower number in cyme, an average of 20 cm in diameter and 7 cm in depth.

*Peduncles*.—Up to 10 cm long and about 3 mm in width, upper surface stained purple N77B in color, lower surface green 144C in color, primarily glabrous surface.

*Pedicels*.—Up to 8 cm long and about 2 mm in width, upper surface green 144C and heavily suffused with purple N77B in color, lower surface green 144C in color, glabrous but sparsely hairy towards flower.

*Flower bud description*.—Nodding, lanceolate, apex acuminate, ribbed, green at base (157A) with a bit of purple (85C) at the apex.

*Flower fragrance*.—None.

*Lastingness of the flowers*.—Individual flowers last up to about 7 days until the first tepal drop followed later by the stamens.

*Flower quantity*.—About 200 flowers on an established plant.

*Flower type*.—Star shaped and almost spreading.

*Flower aspect*.—More or less upright.

*Flower size*.—Ranges from 5 to 10 cm in diameter, about 2 cm in depth.

*Flower sex*.—Bisexual.

*Tepal number*.—4, 5 or 6.

*Tepal shape*.—Obovate to oblanceolate or elliptic.

*Tepal apex*.—Acute.

*Tepal base*.—Cuneate.

*Tepal margin*.—Entire.

*Tepal surface*.—Glabrous on both sides.

*Tepal color*.—Upper surface white (whiter than 155A) in color, especially in cold weather suffused with a bit purple-violet 85C at in the middle, lower surface white in color (whiter than 155A) with a bit purple 85C at the apex and greenish base 145C, fading to pure white (whiter than 155A).

*Tepal size*.—Up to 5.5 cm in length and 3 cm in width.

Reproductive organs:

*Gynoecium*.—Numerous pistils (20 to 30), 1.2 cm in length, ovary superior and green (145C) in color, style lower half silvery 198D plumose, upper half glabrous and dark red-purple 59B in color including the stigma.

*Androcoecium*.—Stamens (about 20 to 30), filaments 0.4 to 0.9 cm long and 0.05 cm in width, linear, pale green 145B in color with white base, anthers up to 0.4 cm long and 0.05 cm in width, linear, cream 158D to dull purple 76D in color with grayish (202D) pollen, connective dull pale purple 76D in color with dark purple N79B and acute tip.

*Seed*.—Usually sterile, hardly no seed is set but when so; achene green (144B) in color and margined, style up to 2.5 cm long, sparsely hairy at the base but otherwise glabrous and green (137C) flushed with purple (59B) in color.

It is claimed:

1. A new and distinct cultivar of *Clematis* plant named 'Zofofri' as herein illustrated and described.

* * * * *